United States Patent
Tojo et al.

(10) Patent No.: US 9,903,709 B2
(45) Date of Patent: Feb. 27, 2018

(54) INSERTION PORTION DETECTION DEVICE AND INSERTION PORTION DETECTION SYSTEM

(71) Applicant: OLYMPUS CORPORATION, Tokyo (JP)

(72) Inventors: Ryo Tojo, Hachioji (JP); Eiji Yamamoto, Musashimurayama (JP); Jun Hane, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 613 days.

(21) Appl. No.: 14/445,722

(22) Filed: Jul. 29, 2014

(65) Prior Publication Data

US 2014/0336462 A1    Nov. 13, 2014

Related U.S. Application Data

(63) Continuation of application No. PCT/JP2013/052010, filed on Jan. 30, 2013.

(30) Foreign Application Priority Data

Jan. 31, 2012  (JP) .................................. 2012-018552

(51) Int. Cl.
*A61B 1/00* (2006.01)
*A61B 1/04* (2006.01)
(Continued)

(52) U.S. Cl.
CPC .......... *G01B 11/14* (2013.01); *A61B 1/00009* (2013.01); *A61B 1/0016* (2013.01);
(Continued)

(58) Field of Classification Search
CPC ......... A61B 1/00; A61B 1/04; A61B 1/00009; A61B 1/00073; A61B 1/00133;
(Continued)

(56) References Cited

U.S. PATENT DOCUMENTS

2002/0183601 A1* 12/2002 Tearney ............. A61B 1/00082
  600/310
2008/0009675 A1* 1/2008 Kura .................. A61B 1/00147
  600/137
(Continued)

FOREIGN PATENT DOCUMENTS

CN         101196569 A     6/2008
JP       2005-131318 A     5/2005
(Continued)

OTHER PUBLICATIONS

Chinese Office Action dated Oct. 29, 2015 from related Chinese Patent Application No. 201380007445.6, together with an English language translation.
(Continued)

*Primary Examiner* — Anhtuan T Nguyen
*Assistant Examiner* — William Chou
(74) *Attorney, Agent, or Firm* — Scully, Scott, Murphy & Presser, P.C.

(57) ABSTRACT

An insertion portion detection device provided with a light source unit which emits measuring beam to an outer circumferential surface of a cylindrical shape of an insertion portion to be inserted into an insertion target and to be a detection target, an optical pattern detection unit which receives reflected light from the outer circumferential surface and which sequentially acquires image data in a predetermined range of the outer circumferential surface including given optical patterns so that at least some of the optical patterns correspond to the image data, and a displacement amount calculation unit which detects a corresponding optical pattern from the image data and calculates at least one of an insertion amount of the insertion portion and an amount of rotation around the central axis of the cylindrical shape.

14 Claims, 6 Drawing Sheets

(51) Int. Cl.
| | |
|---|---|
| A61B 1/06 | (2006.01) |
| G01B 11/14 | (2006.01) |
| A61B 1/24 | (2006.01) |
| G01D 5/347 | (2006.01) |
| G01D 5/30 | (2006.01) |

(52) U.S. Cl.
CPC ...... *A61B 1/00073* (2013.01); *A61B 1/00133* (2013.01); *A61B 1/24* (2013.01); *G01D 5/30* (2013.01); *G01D 5/347* (2013.01)

(58) Field of Classification Search
CPC ........ A61B 1/0016; A61B 1/24; G02B 23/24; G02B 23/2415; G02B 23/2461
USPC ........ 600/102, 103, 108, 109, 114, 117, 118, 600/160, 170, 171, 178, 181; 604/19; 606/108
See application file for complete search history.

(56) References Cited

U.S. PATENT DOCUMENTS

| | | | |
|---|---|---|---|
| 2008/0140324 A1 | 6/2008 | Torii et al. | |
| 2011/0071355 A1* | 3/2011 | Kura | A61B 1/00147 600/118 |
| 2012/0302828 A1* | 11/2012 | Toledo-Crow | A61B 18/24 600/108 |

FOREIGN PATENT DOCUMENTS

| | | |
|---|---|---|
| JP | 2005-185308 A | 7/2005 |
| JP | 2006-230620 A | 9/2006 |
| JP | 2009-077765 A | 4/2009 |
| JP | 2011-099799 A | 5/2011 |

OTHER PUBLICATIONS

Japanese Office Action dated Aug. 16, 2016 in related Japanese Patent Application No. 2013-556456.

English translation of International Preliminary Report on Patentability together with the Written Opinion dated Aug. 14, 2014 received in related International Application No. PCT/JP2013/052010.

International Search Report dated May 7, 2013 issued in PCT/JP2013/052010.

Chinese Office Action dated Feb. 3, 2017 in Chinese Patent Application No. 201380007445.6.

* cited by examiner

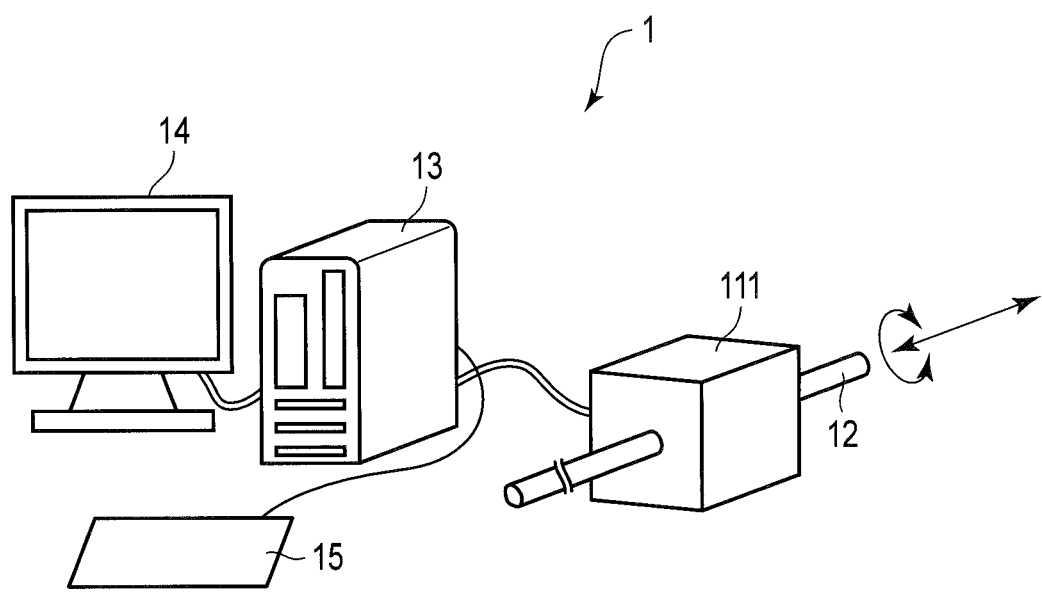
F I G. 1
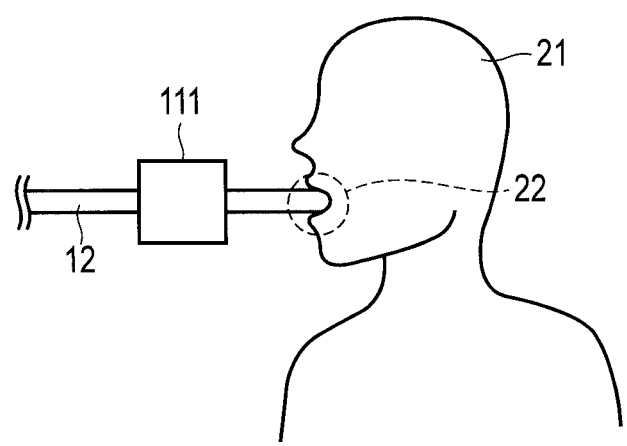
F I G. 2

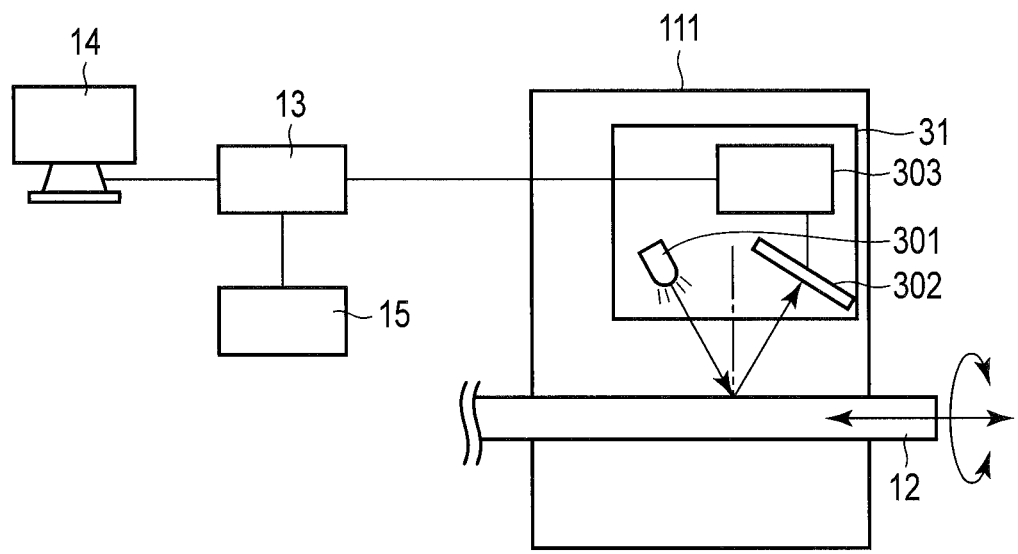
F I G. 3
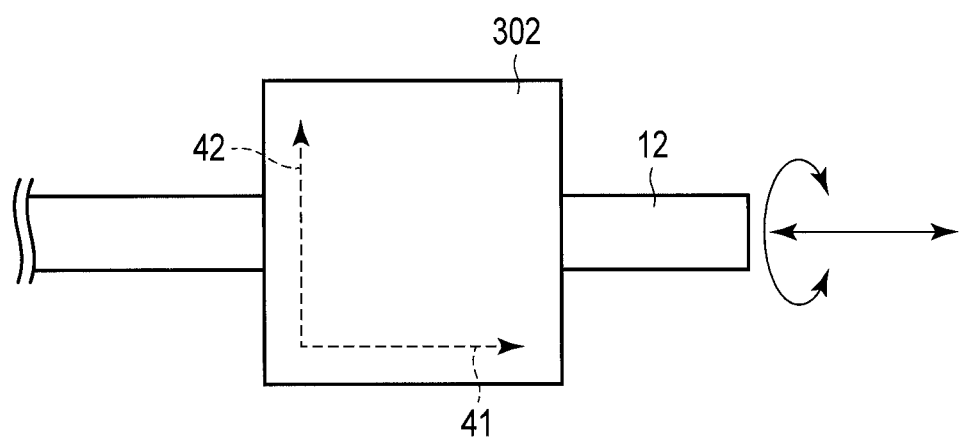
F I G. 4

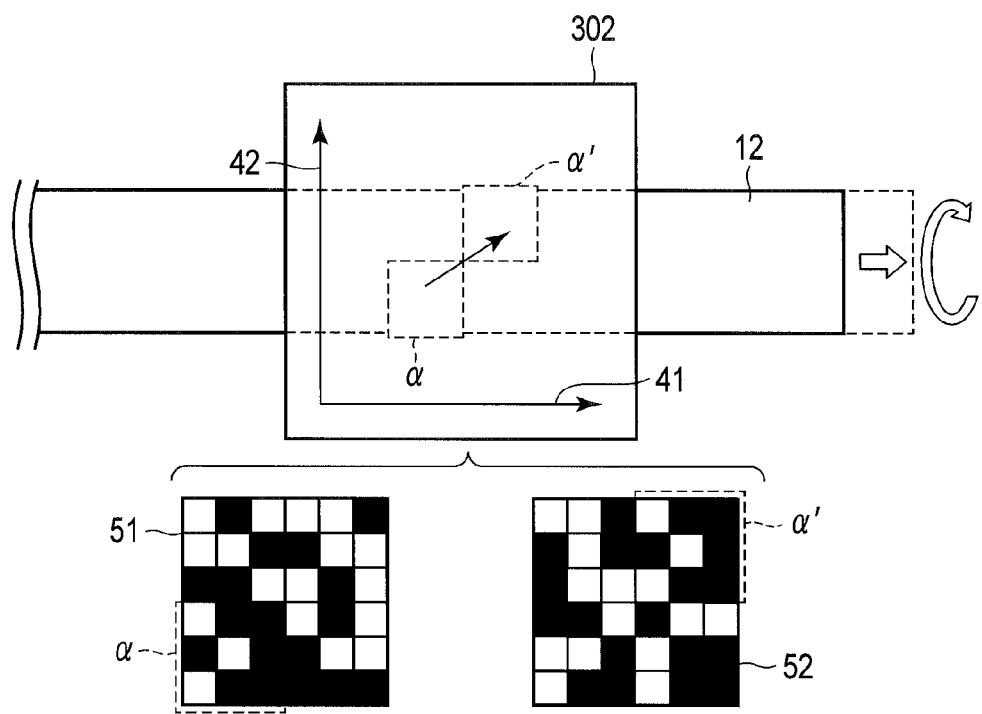
F I G. 5
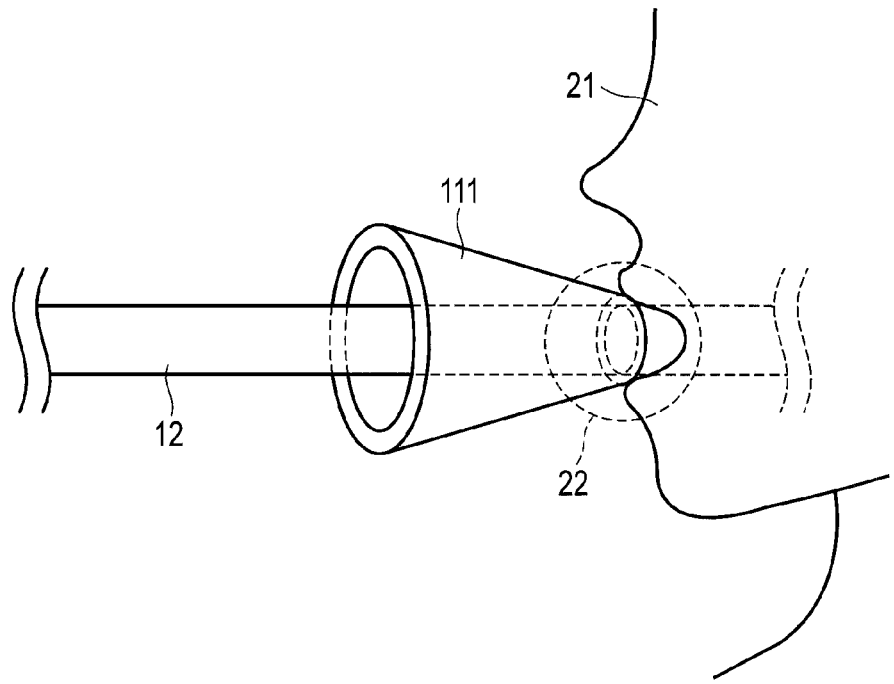
F I G. 6

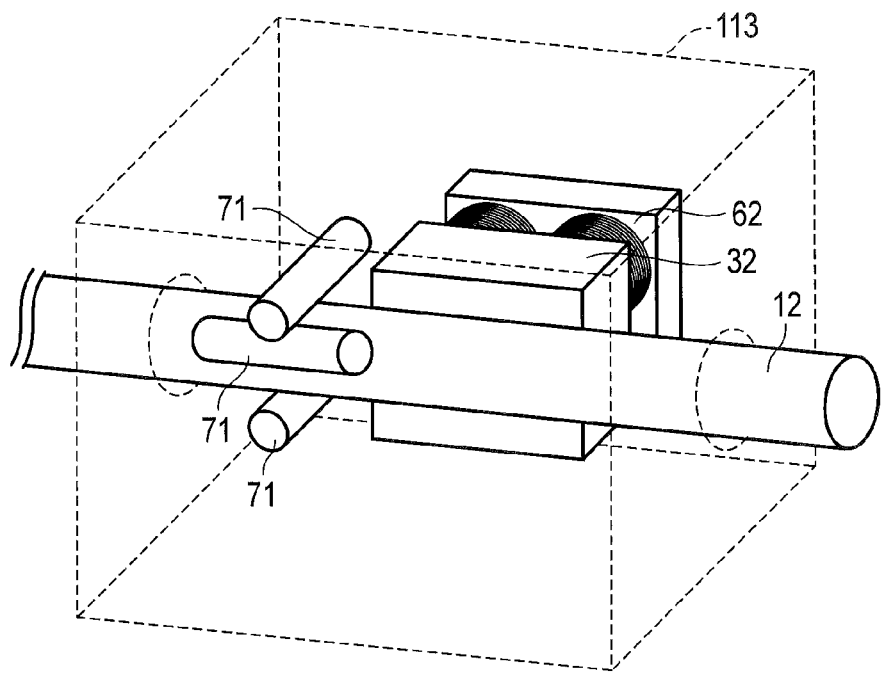
F I G. 8A
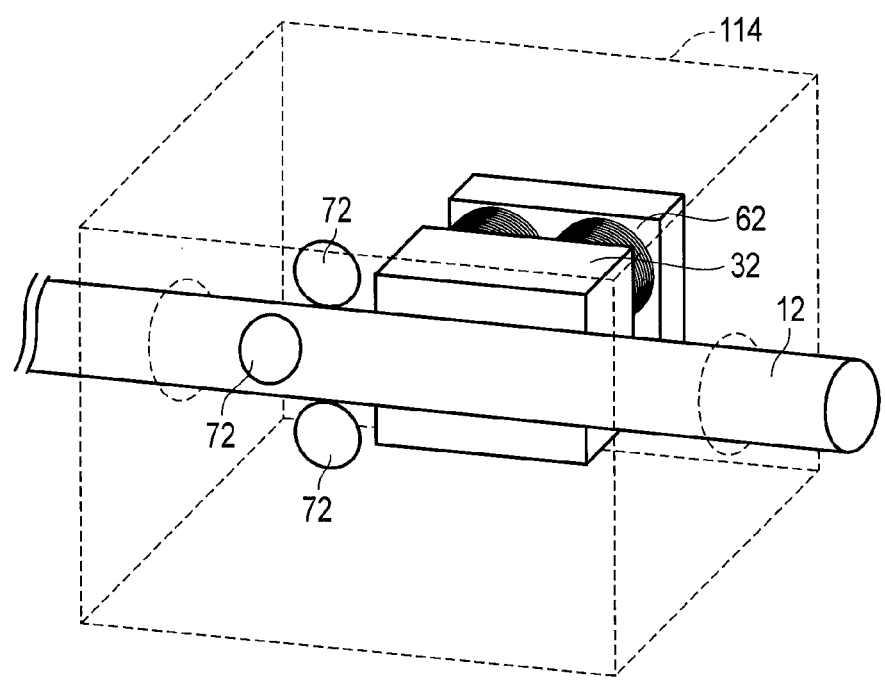
F I G. 8B

INSERTION PORTION DETECTION DEVICE AND INSERTION PORTION DETECTION SYSTEM

CROSS-REFERENCE TO RELATED APPLICATIONS

This is a Continuation application of PCT Application No. PCT/JP2013/052010, filed Jan. 30, 2013, which was published under PCT Article 21(2) in Japanese. This application is based upon and claims the benefit of priority from prior the Japanese Patent Application No. 2012-018552, filed Jan. 31, 2012 the entire contents of which are incorporated herein by references.

BACKGROUND OF THE INVENTION

1. Field of the Invention

The present invention relates to a detection device and an insertion portion detection system which detect an insertion amount of an insertion portion having a cylindrical shape, and an amount of rotation around the central axis of the cylindrical shape.

2. Description of the Related Art

In general, it is necessary to detect an insertion amount when inserting an insertion portion of, for example, an endoscope device into an insertion target. For example, Jpn. Pat. Appln. KOKAI Publication No. 2005-185308 has suggested a system comprising at least a roller disposed in an insertion assist tool, and a sensor which detects the number of rotations of the roller, to detect the relative amount of the insertion of the insertion portion into the insertion assist tool.

In this configuration, the roller rotates while being in contact with the outer circumferential surface of the insertion portion, and the number of rotations of the roller is detected to calculate an insertion amount. As another embodiment, there is also a description of a system in which optical indexes or magnetic indexes are attached to the insertion portion and are read by an optical sensor or a magnetic sensor to detect an insertion amount.

SUMMARY OF INVENTION

However, the detection by the roller suggested in Jpn. Pat. Appln. KOKAI Publication No. 2005-185308 may become impossible because the roller slides on the outer circumferential surface of the insertion portion without rotating or because an error occurs in the detection as a result of the separation between the roller and the outer circumferential surface of the insertion portion. On the other hand, the noncontact detection system which uses the optical sensor or the magnetic sensor requires the optical indexes or magnetic indexes to be newly provided in the insertion portion, and it is not easy to mount this system on endoscope devices that are already available on the market.

BRIEF SUMMARY OF THE INVENTION

According to an embodiment of the present invention, there is provided an insertion portion detection device provided with a sensor unit comprising: a light source unit which emits measuring beam measuring beam to an outer circumferential surface of a cylindrical shape of an insertion portion to be inserted into an insertion target and to be a detection target, an optical pattern detection unit which receives reflected light from the outer circumferential surface and which sequentially acquires image data in a predetermined range of the outer circumferential surface including given optical patterns so that at least some of the optical patterns correspond to the image data, and a displacement amount calculation unit which detects a corresponding optical pattern from the image data and calculates at least one of an insertion amount of the insertion portion and an amount of rotation around the central axis of the cylindrical shape.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 1 is a perspective view of an insertion portion detection system according to a first embodiment;

FIG. 2 is a layout plan of an insertion portion detection device of the insertion portion detection system;

FIG. 3 is a configuration diagram of an insertion portion detection device;

FIG. 4 is a schematic diagram of an optical pattern detector;

FIG. 5 is a diagram showing the displacement of a reference pattern;

FIG. 6 is a diagram showing an insertion portion which is directly inserted into an insertion target;

FIG. 8A is a perspective view of an insertion portion detection device having cylindrical position limiters;

FIG. 8B is a perspective view of an insertion portion detection device having spherical position limiters.

DETAILED DESCRIPTION OF THE PREFERRED EMBODIMENT

Figure 7:
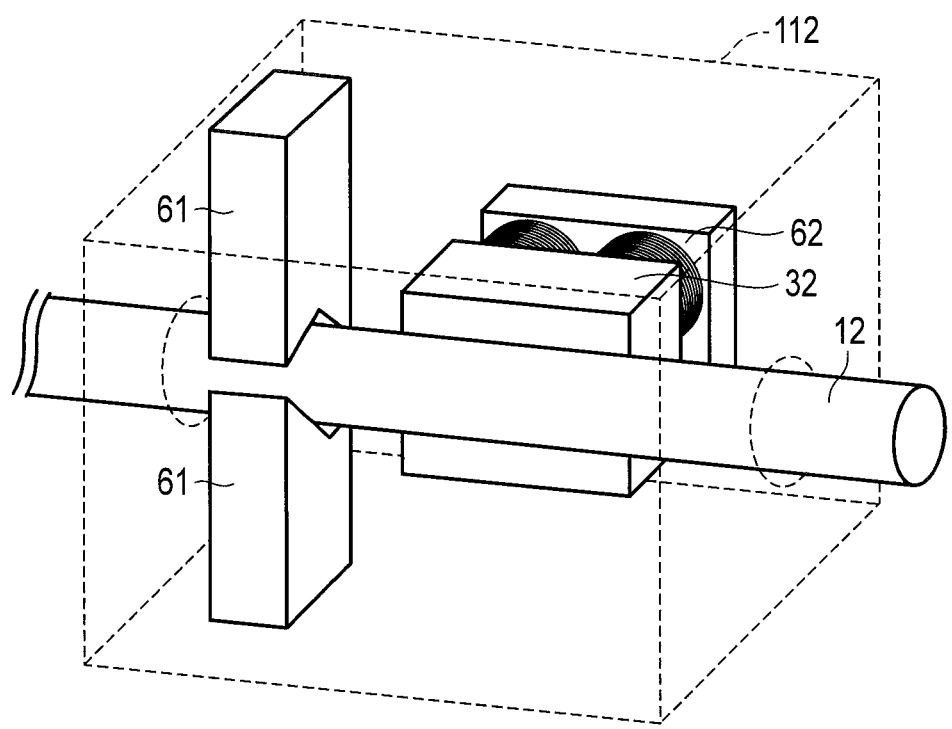
FIG. 7 is a perspective view of an insertion portion detection device according to a second embodiment.

Hereinafter, embodiments of the present invention will be described in detail with reference to the drawings.

First Embodiment

FIG. 1 is a perspective view of an insertion portion detection system 1 according to the first embodiment. FIG. 2 shows an example of the layout of the insertion portion detection device 111 of the insertion portion detection system 1.

The insertion portion detection system 1 has an insertion portion detection device 111 which detects a dynamic insertion amount and/or rotation amount of an insertion portion, a control unit 13 which processes and analyzes data acquired in the insertion portion detection device 111, a monitor 14 which displays results processed in the control unit 13, and an input unit 15 for an operator to input an instruction to the control unit 13. As shown in FIG. 2, the insertion portion detection device ill is disposed in the vicinity of an insertion hole 22 of an insertion target 21 so that a relative position (space) does not change between the insertion portion detection device 111 and the insertion hole 22. For example, in this case, the insertion portion detection device 111 and the insertion hole 22 are disposed so that the position of one of them is a reference position and so that the position of the other does not change.

The amount of the insertion of an insertion portion 12 into the insertion target 21 and/or the rotation amount of the insertion portion 12 are/is detected on the basis of the disposition of the insertion portion detection device 111 or on the basis of the insertion hole 22.

As shown in FIG. 1, the control unit 13 is connected to the later-described insertion portion detection device 111, the monitor 14, and the input unit 15 by, for example, wiring lines, and sends and receives electric signals to and from these components. The control unit 13 analyzes and processes data acquired in the later-described insertion portion detection device 111, and sends the results to the monitor 14 as an electric signal. The monitor 14 displays the results on a screen. In this instance, the operator inputs an instruction for desired analysis and processing on the input unit 15, and can thereby handle the operation of the control unit 13. For example, the control unit 13 is a personal computer.

The insertion portion 12 is a long component. For example, the insertion portion 12 has a long cylindrical component, and the diameter of its section is 2 mm to 20 mm. By way of example, the insertion portion 12 is an insertion portion of a treatment instrument such as a flexible or rigid endoscope body, a manipulator, or a catheter, and is inserted into a living tissue in use or is inserted into a structure in use, as is the case with an industrial endoscope. The insertion portion 12 may be a combination of the insertion portions of the endoscope body and the treatment instrument. Hereinafter, the insertion portion 12 is described as an insertion portion of an endoscope.

FIG. 3 is a configuration diagram of the insertion portion detection device 111.

The insertion portion detection device 111 has at least a sensor unit 31 stored in a housing. As shown in FIG. 3, the sensor unit 31 has a light source unit 301 which applies light (measuring beam) to the insertion portion 12, an optical pattern detection unit 302 which acquires an optical pattern of the insertion portion 12, and a displacement amount calculation unit 303 which calculates a displacement amount.

The sensor unit 31 receives part of the light reflected on the outer circumference of the insertion portion 12 by a light receiving element of the optical pattern detector 302, and sequentially acquires image data in a predetermined range so that at least some of the optical patterns correspond to the image data. The displacement amount calculation unit 303 has functions to select some target optical patterns of any one of the acquired image data, detect an optical pattern corresponding to the target optical patterns from the image data after the elapse of a given length of time, and calculate a displacement amount from the movement amount of the target optical pattern on the image. Here, the predetermined range is a range or a region which permits imaging and detection by the optical pattern detection unit 302 that is an imaging device. The insertion portion detection device 111 may have no housing. Hereinafter, the optical pattern targeted in the image of given image data is referred to as a reference pattern. The time in which the image data is obtained is referred to as a detection time. The optical pattern detector 302 may successively acquire image data in the predetermined range, and the displacement amount calculation unit 303 may have a function to detect a corresponding optical pattern from the image data.

The light source unit 301 is disposed so that a light flux is emitted to the outer circumferential surface (target detection region) of the insertion portion 12 having a cylindrical shape to be a detection target and so that part of the light reflected on the outer circumferential surface enters the optical pattern detection unit 302. A collection lens is disposed between the light source unit 301 and the insertion portion 12 so that the light emitted from the light source unit 301 is efficiently applied to the outer circumferential surface of the insertion portion 12 (not shown). Hereinafter, the light applied from the light source unit or the light flux is referred to as the measuring beam. For example, the light source unit 301 is a light source which emits coherent light as the measuring beam, and is an LED or a laser light source. In the present embodiment, the light source unit 301 is described as the laser light source.

The coherent light has a phase correlation, and can therefore produce a clear phase difference in the reflected light even if an object to be irradiated has small depressions and projections. For example, the use of the coherent light permits clear image data regarding a glossy smooth surface to be acquired even when the coherent light is applied to the smooth surface. That is, the use of the coherent light permits information regarding the outer circumferential surface of the insertion portion 12 to be acquired as a clear optical pattern. The optical pattern is, for example, a speckle pattern.

FIG. 4 is a schematic diagram of the optical pattern detection unit 302.

An objective lens is disposed between the optical pattern detection unit 302 and the insertion portion 12 so that the measuring beam reflected on the outer circumferential surface of the insertion portion 12 is focused on a light receiving surface of the optical pattern detection unit 302 (not shown).

The optical pattern detection unit 302 has an image pickup device in which light receiving elements are at least two-dimensionally arrayed. For example, the optical pattern detection unit 302 has an image pickup device in which light receiving elements are arrayed in matrix form. The image pickup device is, for example, a CCD or C-MOS image sensor. As shown in FIG. 4, an axis along the direction parallel to an insertion direction in the optical pattern detection unit 302 is an x-axis 41, and an axis that intersects at right angles with the x-axis 41 is a y-axis 42.

The optical pattern detection unit 302 has a function to successively image, as image data, at least information regarding the smooth surface having a curvature and process the image data. That is, the optical pattern detection unit 302 has a function to successively image the predetermined range (target detection region) of the outer circumferential surface of the insertion portion 12 including given optical patterns, process the images, and output the optical pattern of the outer circumferential surface as the image data. The optical pattern detection unit 302 is not exclusively capable of processing in accordance with the shape of the outer circumferential surface. For example, the optical pattern detection unit 302 can even process information regarding a plane having depressions and projections as the image data.

The optical pattern detection unit 302 is connected to the displacement amount calculation unit 303, and sends the detected image data thereto. For example, the optical pattern detection unit 302 sends, to the displacement amount calculation unit 303, the image data successively obtained at given detection times $t_1, t_2 \ldots t_n \ldots$ so that the detection time at the start of detection is $t_0$.

The displacement amount calculation unit 303 is connected to the control unit 13, and is driven and controlled by the control unit 13. The displacement amount calculation unit 303 has what is known as a pattern matching function to select a given reference pattern existing in part of the image in the image data obtained by the optical pattern detection unit 302, detect an optical pattern corresponding to the reference pattern from given image data among the image data after the elapse of a given length of time, and calculate a displacement amount between these optical patterns in the image. Here, the range of the optical patterns to be detected can be adjusted.

Furthermore, the displacement amount calculation unit 303 has a function to calculate a movement amount of the insertion portion 12 in the insertion direction and an amount of rotation around the central axis of the cylindrical shape from the displacement amount of the reference pattern in the image data.

FIG. 5 is a diagram showing the displacement of the reference pattern.

As shown in FIG. 5, the displacement amount calculation unit 303 compares displacements in the image data regarding any selected reference pattern α existing in the image of image data 51 obtained at any time $t_{n-1}$ by the optical pattern detection unit 302, a reference pattern α existing in part of the image of image data 52 obtained at the time $t_n$ after the elapse of a given length of time from the time $t_{n-1}$, and a corresponding optical pattern α'. The displacement amount calculation unit 303 then calculates displacement amounts in the direction of the x-axis 41 and the direction of the y-axis 42. Therefore, the displacement amount calculation unit 303 can add up the displacement amounts of the reference pattern at given successive times, and calculate the insertion amount of the insertion portion 12 and the rotation amount from a given detection time to a desired detection time.

The process of calculating the insertion amount and the rotation amount from the above-mentioned displacement amount of the reference pattern on the image data requires a coefficient in each direction for previous conversion from the displacement amount of the reference pattern on the image data to the insertion amount and the rotation amount. Therefore, the insertion amount and the rotation amount are calculated by multiplying a displacement amount of each of the coordinates by each coefficient. The calculated results can be selectively output regarding a desired direction. Equation 1 which is a calculation formula of the insertion amount and Equation 2 which is a calculation formula of the rotation amount are shown below. That is, the displacement amount calculation unit 303 repeats the processing described above, adds up the displacement amounts of the coordinates at the given successive detection times, and thereby calculates the insertion amount and rotation amount of the insertion portion 12 from a given detection time to a desired detection time.

$$\Delta L = \alpha \times \Delta x \qquad \text{Equation 1}$$

wherein $\Delta L$ is an insertion amount from the time $t_{n-1}$ to the time $t_n$, $\Delta x$ is a coordinate difference of the corresponding patterns of the image data from the time $t_{n-1}$ to the time $t_n$ in the direction of the x-axis 41, and α is an insertion amount conversion coefficient.

$$\Delta \theta = \beta \times \Delta y \qquad \text{Equation 2}$$

wherein $\Delta\theta$ is the rotation amount from the time $t_{n-1}$ to the time $t_n$, $\Delta y$ is a coordinate difference of the corresponding patterns of the image data at the time $t_{n-1}$ and the time $t_n$ in the direction of the y-axis 42, and β is an insertion amount conversion coefficient.

In the present embodiment, when the detection is started, coherent light is applied to the outer circumferential surface of the insertion portion 12 from the light source unit 301. The applied coherent light is reflected on the outer circumferential surface, and part of the reflected light enters the optical pattern detection unit 302. The optical pattern detection unit 302 images an optical pattern at a given detection time, and outputs the image as image data. In this instance, image data are successively acquired at given detection times $t_0, t_1, t_2 \ldots t_n \ldots$. The acquired image data are sent to the displacement amount calculation unit 303.

The displacement amount calculation unit 303 determines at least one reference pattern existing in the image of the image data obtained at a given detection time, and detects an optical pattern corresponding to the reference pattern from the image of the image data after the elapse of a given length of time from the detection time. The displacement amount calculation unit 303 also calculates displacement amounts in the directions along the x-axis 41 and the y-axis 42 from the displacements of the optical patterns in the image. The calculated displacement amounts of the coordinates along the axes are converted to an insertion amount and a rotation amount.

In a similar manner, displacement amounts are calculated between given times, for example, between the time $t_1$ and the time $t_2$, between the time $t_2$ and the time $t_3$, ... between the time $t_{n-1}$ and the time $t_n$. The displacement amounts between the successive times of the reference pattern are then added up, and a movement amount and a rotation amount of the insertion portion 12 from the position of the detection time $t_0$ at which the detection has been started to the position of the detection time $t_n$ at which the detection has finished are calculated. The movement amount and the rotation amount of the insertion portion 12 at any time interval can be calculated.

According to the present embodiment, the insertion portion detection device 111 has functions to successively image, as image data, at least information regarding the smooth surface having a curvature and process the image data by the sensor unit 31, and can detect an optical pattern corresponding to the reference pattern from the image data obtained at a given time, and calculate an insertion amount and a rotation amount of the insertion portion 12 from the displacement amounts of the patterns. Thus, a user can selectively output processing results of the insertion amount and/or the rotation amount of the insertion portion 12. Therefore, the insertion portion detection device 111 according to the present embodiment can correctly detect the insertion amount and/or the rotation amount without the fabrication of the insertion portion 12 or the addition of new components to the insertion portion 12.

According to the present embodiment, coherent light is used as the measuring beam applied from a light source 6. Therefore, even if the depressions and projections on the outer circumferential surface of the insertion portion 12 are so small that contrast is not easily produced in the optical pattern when incoherent light is applied, a phase difference is produced when the coherent light is reflected on the outer circumferential surface of the insertion portion 12, and a figure which is enhanced to the degree that the contrast can be clearly recognized can be generated. That is, a speckle pattern can be generated, and optical pattern detection means detects the speckle pattern, so that optical patterns that cannot be easily detected with the incoherent light can be easily detected. The sensor unit 31 provided in the insertion portion detection device 111 can simultaneously detect the displacements of the optical pattern of the insertion portion 12 in the directions along the x-axis 41 and the y-axis 42 by the imaging device. Therefore, the insertion portion detection device 111 does not require more than one sensor unit for detecting the respective directions to be disposed therein. Thus, the insertion portion detection device 111 can be, for example, reduced in size.

Furthermore, when the insertion portion detection device 111 is disposed in alignment with or in the vicinity of the insertion hole 22 so that the relative position (space) does not change, errors in the amount of the insertion of the insertion portion detection device 111 into the insertion target 21, and/or the rotation amount are reduced.

When the present embodiment is applied to a flexible endoscope, flexure is caused between the insertion portion detection device 111 and the insertion hole 22 during the insertion into the insertion target 21 in the situation where the distal end of the flexible endoscope is not propelled, for example, due to collision with some part of the insertion target. This flexure causes errors in the insertion amount and/or the rotation amount. Thus, the insertion portion detection device 111 may be configured to be at least partly inserted into the insertion hole 22 of the insertion target 21 in the same manner as a mouthpiece. For example, as shown in FIG. 6, the insertion portion detection device 111 may be in the shape of a conical trapezoid. In this case, the space between the insertion portion detection device 111 and the insertion hole 22 is eliminated. Therefore, the locations of the insertion portion detection device 111 and the insertion hole 22 substantially correspond to each other, so that errors in the insertion amount and/or the rotation amount caused by the flexure can be reduced.

Second Embodiment

FIG. 7 is a perspective view of an insertion portion detection device 112 according to the second embodiment. The present embodiment is substantially similar in configuration to the insertion portion detection system 1 according to the first embodiment, and is different in the configuration of the insertion portion detection device 112. Therefore, in the present embodiment, components equivalent to those in the first embodiment are indicated by the same reference numbers and are not described.

As shown in FIG. 7, the insertion portion detection device 112 according to the present embodiment has a sensor unit 32, position limiters 61, and a sensor distance maintaining unit 62. The sensor unit 32 has a configuration equivalent to that of the sensor unit 31 according to the first embodiment. Therefore, the sensor unit 32 has a light source unit 301, an optical pattern detection unit 302 which images an insertion portion, and a displacement amount calculation unit 303 which calculates a displacement amount. These units are stored in a housing. For example, although not shown, the insertion portion detection device 112 is connected to a control unit 13 by, for example, a wiring line, in the same manner as the insertion portion detection device according to the first embodiment.

The position limiters 61 are disposed to hold an insertion portion 12 in between to limit a considerable displacement of the insertion portion 12. As shown in FIG. 7, the position limiters 61 are paired, and hold the insertion portion 12 in between from opposite positions, for example, from the top and the bottom. The position limiters 61 are provided with V-shaped groove structures along the insertion direction of the insertion portion 12, and regulate the lateral movement of the insertion portion 12. For example, the position limiters 61 are located on the entrance side of the insertion portion detector 112. More than one position limiter 61 may be disposed. For example, pairs of position limiters 61 may be disposed on the entrance side and the exit side for insertion into the insertion portion detection device 112. Instead of being V-shaped, the groove structure of the position limiter 61 may be, for example, semicircularly shaped or rectangularly shaped as long as the position limiter 61 can regulate the movement of the insertion portion.

The space between each of the position limiters 61 and the insertion portion 12 can be adjusted. For example, the position limiter 61 can be adjusted or moved in a direction perpendicular to the outer circumferential surface of the insertion portion 12 at each location, and can be applied to insertion portions 12 having various diameters. In this instance, the position limiter 61 is fixed by a fixing member to avoid displacement. For example, the position limiter 61 is screwed to the inner wall of the insertion portion detection device 112. The position limiters 61 have a gap to permit the insertion operation of the insertion portion 12 when the insertion portion 12 is held in between. Here, the gap is a clearance formed between a pair of position limiters 61 and the insertion portion 12 when the insertion portion 12 is held in between a pair of position limiters 61. That is, a pair of position limiters 61 hold the insertion portion 12 in between with a slight clearance without completely abutting on the insertion portion 12.

The sensor distance maintaining unit 62 has the sensor unit 32 at the end facing the outer circumference of the insertion portion 12, and is provided at a predetermined position. For example, the sensor distance maintaining unit 62 is a spring structure, and has another end opposite to the former end fixed to the inner wall of the insertion portion detection device 112 with, for example, screws. For example, the distance between the optical pattern detection unit 302 and the outer circumferential surface (target detection region) of the insertion portion 12 is set at 5 mm as a proper distance for detection. Here, the proper distance is a distance at which the insertion amount and the rotation amount of the insertion portion 12 are correctly detected. For example, if the distance between the insertion portion which is a subject and the optical pattern detection unit which substantially performs detection is extremely great or extremely small, light is not focused on a light receiving surface, and correct pattern detection in the image data is impossible. Thus, the proper distance is a distance at which reflected light from the outer circumferential surface (target detection region) of the subject is focused on the light receiving surface of the optical pattern detection unit 302.

As shown in FIG. 7, the sensor unit 32 is bonded to the end of the sensor distance maintaining unit 62 to be pressed against the insertion portion 12. The strength of the force applied by the sensor distance maintaining unit 62 is not so great as to prevent the insertion and rotational operation of the insertion portion 12. That is, the outer circumferential surface of the insertion portion 12 and the sensor unit 32 are not overly separated from each other. The sensor unit 32 may have a clearance formed between the sensor unit 32 and the insertion portion 12 without abutting on the insertion portion 12 within a proper range for detection.

Inside the sensor unit 32, for example, the optical pattern detection unit 302, the displacement amount calculation unit 303, a lens (not shown), and a structure such as a housing to store the sensor unit 32 are arranged at predetermined positions by jigs which arrange these components. Thus, a substantially constant distance is maintained by the sensor distance maintaining unit 62 between the outer circumferential surface (target detection region) of the insertion portion 12 and the optical pattern detection unit 302 which substantially performs detection. That is, the outer circumferential surface of the insertion portion 12 and the optical pattern detection unit 302 do not come too close to each other. Therefore, the sensor unit 32 is maintained at the distance at which the insertion amount and the rotation amount of the insertion portion 12 are correctly detected.

In the present embodiment, as shown in FIG. 7, the insertion portion 12 is inserted from the left side on the drawing. In this instance, the position limiters 61 are adjusted to prevent the inhibition of the insertion and rotation of the insertion portion 12. Thus, when the insertion portion 12 is inserted in the insertion portion detection device 112, the insertion portion 12 is held in between to prevent displacement, and the insertion portion 12 is smoothly inserted and rotated. Therefore, the position limiters 61 limit, to a detectable range, the movement of a region (target detection region) on the outer circumferential surface of the insertion portion where image data is to be acquired by the sensor unit 32, in a direction perpendicular to the direction in which the movement is detected as an insertion amount of the insertion portion. Even if the insertion portion 12 is displaced within a range permitted by the gap of the position limiters 61, the sensor distance maintaining unit 62 functions to maintain the sensor unit 32 and the insertion portion 12 at a proper distance for detection. That is, the sensor distance maintaining unit 62 functions to prevent the sensor unit 32 from being extremely separated from the insertion portion 12, and the optical pattern detection unit (not shown) is disposed at a predetermined position inside the sensor unit 32 to prevent the optical pattern detection unit 302 which substantially performs detection from coming too close to the insertion portion 12. Therefore, the position limiters 61 function to limit at least the movement of the part of the outer circumferential surface of the insertion portion 12 to which the measuring beam is applied, to the range detectable by the sensor unit 32. The sensor distance maintaining unit 62 functions to limit, to the range detectable by the sensor unit 32, at least the distance between the part of the outer circumferential surface of the insertion portion 12 to which the measuring beam is applied and the sensor unit 32.

According to the present embodiment, the distance between the optical pattern detector 302 disposed inside the sensor unit 32 and the outer circumferential surface of the insertion portion 12 is maintained at a proper distance for detection by the position limiters 61 and the sensor distance maintaining unit 62. Therefore, detection failures resulting from the displacement of the insertion portion 12 are reduced. That is, detection errors in the insertion amount and/or the rotation amount of the insertion portion 12 are reduced.

Furthermore, the position limiters 61 can adjust the space between the position limiters 61 and the insertion portion 12 in accordance with the diameter of the insertion portion 12. Therefore, the insertion portion detection device 112 according to the present embodiment can be applied to insertion portions 12 having various diameters, and can properly detect the insertion amount and/or the rotation amount.

Now, a modification of the second embodiment is described.

FIG. 8A is a perspective view of an insertion portion detection device 113 having cylindrical position limiters 71. FIG. 8B is a perspective view of an insertion portion detection device 114 having spherical position limiters 72.

Each of the insertion portion detection devices 113 and 114 according to the modification of the present embodiment is substantially similar to the above-described insertion portion detection device 112 according to the second embodiment, but different in the shapes and locations of the position limiters 71 and 72. Therefore, in the modification of the present embodiment, the same components as those in the second embodiment are indicated by the same reference numbers and are not described.

In FIG. 8A, the position limiters 71 comprising cylindrical members are disposed inside the insertion portion detection device 113 to hold the insertion portion 12 at a proper position for detection. Here, for example, the position limiters 71 are disposed in three parts; upper and lower parts and one side part (the side facing the sensor unit 32) to be in abutment with the outer circumferential surface of the insertion portion 12. These position limiters 71 are disposed without preventing the insertion and/or the rotation of the insertion portion 12. For example, all of the disposed position limiters 71 comprising cylindrical members may be disposed perpendicularly to the insertion portion 12. In the same manner as the position limiters 61 according to the second embodiment, the position limiter 71 also functions to limit at least the movement of the part of the outer circumferential surface (target detection region) of the insertion portion 12 to which the measuring beam is applied, to the range detectable by the sensor unit 32.

In FIG. 8B as well, the position limiters 72 comprising spherical members are disposed inside the insertion portion detection device 114 in the same three parts, and are brought into abutment with the outer circumferential surface of the insertion portion 12 from the upper and lower parts and one side part. These position limiters 72 are disposed without preventing the insertion and the rotation of the insertion portion 12. In the same manner as the position limiters 61 according to the second embodiment, the position limiters 72 also function to limit at least the movement of the part of the outer circumferential surface (target detection region) of the insertion portion 12 to which the measuring beam is applied, to the range detectable by the sensor unit 32.

The position limiters 71 and 72 can be adjusted or moved in a direction perpendicular to the outer circumferential surface of the insertion portion 12 at each location. Thus, the position limiters 71 and 72 can be easily applied to insertion portions 12 having various diameters. The position limiters 71 and 72 rotate around the central axis or with reference to the center if the insertion portion 12 moves in the insertion direction, and send the insertion portion 12 in the insertion direction. In this instance, the position limiters 71 and 72 are fixed by, for example, fixing members to avoid displacement.

According to the modification of the present embodiment, the distance between the optical pattern detector 302 disposed inside the sensor unit 32 and the outer circumferential surface (target detection region) of the insertion portion 12 is maintained at a proper distance for detection by the position limiters 71 and 72. That is, detection failures resulting from the displacement of the insertion portion 12 are reduced. The position limiters 71 and 72 are cylindrical or spherical members which rotate to assist insertion and rotation, so that frictional resistance is reduced. Thus, the insertion performance and rotation performance of the insertion portion 12 improve. It should be noted that the present embodiment and the modification of the present embodiment do not limit the shapes, locations, and number of the position limiters.

Third Embodiment

Figure 9:
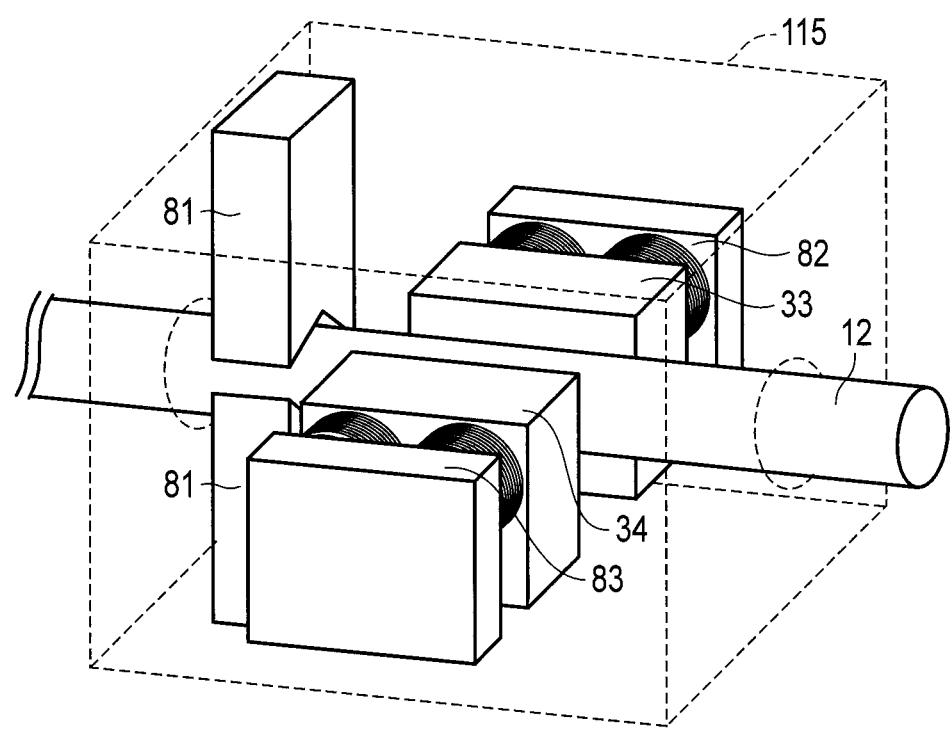
FIG. 9 is a perspective view of an insertion portion detection device according to a third embodiment.

FIG. 9 is a perspective view of an insertion portion detection device 115 according to the third embodiment. The third embodiment is substantially similar in configuration to the insertion portion detection system 1 according to the second embodiment, and is different in the locations of sensor distance maintaining units comprising sensor units. Thus, in the third embodiment, components equivalent to those in the second embodiment are indicated by the same reference numbers and are not described.

As shown in FIG. 9, the insertion portion detection device 115 according to the present embodiment has first and second sensor units 33 and 34, position limiters 81, and first and second sensor distance maintaining units 82 and 83. For example, each of the first and second sensor distance maintaining units 82 and 83 is a spring structure. Both of these first and second sensor units 33 and 34 have configurations equivalent to that of the sensor unit 31 according to the first embodiment. Therefore, each of the first and second sensor units 33 and 34 has a light source unit 301, an optical pattern detection unit 302 which images an insertion portion, and a displacement amount calculation unit 303 which calculates a displacement amount. These units are stored in a housing. For example, although not shown, the insertion portion detection device 115 is connected to a control unit by, for example, a wiring line, in the same manner as the insertion portion detection device according to the first embodiment.

The position limiter 81 has a configuration equivalent to that of the position limiter 61 according to the second embodiment.

Therefore, each of a pair of position limiters 81 can be adjusted or moved in a direction perpendicular to the outer circumferential surface of the insertion portion 12, for example, in an upward/downward direction, and can also be applied to insertion portions 12 having various diameters. In this instance, the position limiters 81 are fixed by, for example, fixing members to avoid displacement. For example, the position limiters 81 are screwed to the inner wall of the insertion portion detection device 115. In the same manner as the position limiters 61, the position limiters 81 have a gap to permit the insertion operation of the insertion portion 12 when the insertion portion 12 is held. The position limiters 81 also hold the insertion portion 12 in between with a slight gap without completely abutting on the insertion portion 12. Regarding the first and second sensor units 33 and 34 and the sensor distance maintaining units 82 and 83, three or more combinations of sensor units and sensor distance maintaining units may be disposed. More than one pair of position limiters 81 may be disposed. As has been shown in the modification of the second embodiment, the position limiter 81 may have a cylindrical shape, a spherical shape, or any shape that can maintain the insertion portion in a proper range for detection.

In the present embodiment, the first sensor unit 33 and the second sensor unit 34 are bonded to the ends of the sensor distance maintaining units 82 and 83 to be pressed against the outer circumferential surface of the insertion portion 12. For example, as shown in FIG. 9, the first sensor unit and the second sensor unit are disposed to face each other across the insertion portion 12. The strength of the force applied by each of the sensor distance maintaining units 82 and 83 is not so great as to prevent the insertion and rotational operation of the insertion portion 12. That is, the outer circumferential surface of the insertion portion 12 is not overly separated from each of the sensor units 33 and 34. Each of the first and second sensor units 33 and 34 may have a clearance formed between each of the sensor units 33 and 34 and the insertion portion 12 without abutting on the insertion portion 12 within a proper range for detection.

Inside each of the sensor units 33 and 34 are arranged for example, the optical pattern detection unit 302, the displacement amount calculation unit 303, and a lens (not shown) at predetermined positions by jigs. Thus, a substantially constant distance is maintained by each of the sensor distance maintaining units 82 and 83 between the outer circumferential surface (target detection region) of the insertion portion 12 and each optical pattern detection unit 302 which substantially performs detection. That is, the outer circumferential surface of the insertion portion 12 and the optical pattern detection unit 302 do not come too close to each other. Therefore, the sensor unit 32 is maintained at the distance at which the insertion amount and the rotation amount of the insertion portion 12 are correctly detected.

In the present embodiment, as shown in FIG. 9, the insertion portion 12 is inserted from the left side on the drawing. In this instance, the position limiters 81 are disposed without preventing the insertion and rotation of the insertion portion 12. Thus, when the insertion portion 12 is inserted in the insertion portion detection device 115, the insertion portion 12 is held in between to prevent displacement, and the insertion portion 12 is smoothly inserted and rotated. Even if the insertion portion 12 is displaced within a range permitted by the gap of the position limiters 81, each of the sensor distance maintaining units 82 and 83 functions to maintain at least one of the sensor units 33 and 34 and the outer circumferential surface (target detection region) of the insertion portion 12 at a proper distance for detection. That is, each of the sensor distance maintaining units 82 and 83 functions to prevent each of the sensor units 33 and 34 from being extremely separated from the insertion portion 12, and the optical pattern detection unit 302 is disposed at a predetermined position inside each of the sensor units 33 and 34 to prevent the optical pattern detection unit 302 which substantially performs detection from coming too close to the insertion portion 12. That is, the position limiters 81 function to limit at least the movement of the part of the outer circumferential surface (target detection region) of the insertion portion 12 to which the measuring beam is applied, to the range detectable by each of the sensor units 33 and 34. Each of the sensor distance maintaining units 82 and 83 functions to limit, to the range detectable by each of the sensor units 33 and 34, at least the distance between the part of the outer circumferential surface (target detection region) of the insertion portion 12 to which the measuring beam is applied and each of the sensor units 33 and 34.

According to the present embodiment, the distance between each of the optical pattern detectors 302 disposed inside each of the sensor units 33 and 34 and the outer circumferential surface (target detection region) of the insertion portion 12 is maintained at a proper distance for detection by each of the position limiters 81 and each of the sensor distance maintaining units 82 and 83.

Therefore, detection failures resulting from the displacement of the insertion portion 12 are reduced. That is, detection errors in the insertion amount and/or the rotation amount of the insertion portion 12 are reduced.

Moreover, the sensor units 33 and 34 are disposed, so that even if the part of the outer circumferential surface of the insertion portion 12 to which the coherent light has been applied is smooth and does not allow sufficient reflected light to be obtained, the sensor units 33 and 34 can assist each other in detection. Thus, errors caused by detection failures in each of the sensor units 33 and 34 can be reduced, and the permissible range of the displacement of the insertion portion 12 is expanded. It is possible to acquire a more correct detection value by comparing the detection values of the first and second sensor units 33 and 34.

The embodiments described above provide an insertion portion detection system in which errors in the detection of the insertion amount and/or the rotation amount of an insertion portion are reduced and which can be used in a general-purpose endoscope.

Although the light source unit is a coherent light source unit in the embodiments described above, the light source unit may be an incoherent light source unit. In the embodiments described above, the optical pattern detector can also detect an optical pattern generated by incoherent light. Therefore, an insertion portion detection device comprising a sensor unit having the incoherent light source unit can detect the insertion amount and/or the rotation amount. The incoherent light source unit is generally inexpensive, and can therefore reduce costs.

In the embodiments described above, the displacement amount calculation unit may be disposed outside the sensor unit. For example, the control unit may double as the displacement amount calculator. As a result, the sensor unit can be, for example, reduced in size.

The embodiments described above do not limit the number, locations, and shapes of the components.

The embodiments of the present invention described above cover the scope of the following additional statements.

[1] An insertion portion detection system characterized by comprising an input unit to input an instruction, a control unit which performs processing under the instruction from the input unit, a monitor which displays data processed in the control unit, and an insertion portion detection device which detects an insertion portion having a cylindrical shape to be a detection target, the insertion portion detection device including a sensor unit, the sensor unit comprising an optical pattern detection unit which receives reflected light from an outer circumferential surface and which sequentially acquires image data in a predetermined range of the outer circumferential surface including given optical patterns so that at least some of the optical patterns correspond to the image data, and a displacement amount calculation unit which detects a corresponding optical pattern from the image data and calculates at least one of an insertion amount of the insertion portion and an amount of rotation around the central axis of the cylindrical shape.

[2] The insertion portion detection system according to (1), characterized in that the insertion portion detection device simultaneously detects the insertion amount and the rotation amount of the insertion portion.

[3] The insertion portion detection system according to (1) or (2), characterized in that measuring beam emitted from a light source unit is coherent light.

[4] The insertion portion detection system according to (1) or (3), characterized in that the optical pattern detection unit acquires a speckle pattern from the image data.

[5] The insertion portion detection system according to any one of (1) to (4), characterized in that the optical pattern detection unit has an imaging device in which light receiving elements are arrayed in matrix form in a two-dimensional direction.

[6] The insertion portion detection system according to (1), characterized by being disposed in alignment with or in the vicinity of an insertion hole of an insertion target.

[7] The insertion portion detection system according to (1), characterized by comprising an opening to pass the insertion portion, wherein at least part of the opening is inserted in an insertion hole of an insertion target, or the opening and the insertion hole of the insertion target are located close to each other in an insertion axis direction.

[8] The insertion portion detection system according to (1), characterized by comprising one or more position limiters configured to limit, to a range detectable by the sensor unit, movement of a target detection region in a direction perpendicular to the direction in which the movement is detected as an insertion amount of the insertion portion, the target detection region being a region on the outer circumferential surface of the insertion portion where the image data is to be acquired.

[9] The insertion portion detection system according to (8), characterized in that the position limiters have shapes to hold the insertion portion in between, a shape suitable for the shape of the insertion portion to be inserted is selected from the shapes of the position limiters, and the position limiters limit the movement of the target detection region by catching the insertion portion from at least two opposite positions.

[10] The insertion portion detection system according to claim (8) or (9), characterized in that the position limiters are adjustable to the diameter of the insertion portion.

[11] The insertion portion detection system according to (1), characterized by comprising a sensor distance maintaining unit configured to adjust the location of the sensor unit to maintain the distance between the optical pattern detection unit and the target detection region within a range detectable by the sensor unit.

[12] The insertion portion detection system according to (11), characterized in that the sensor distance maintaining unit is a spring structure which moves the sensor unit to the detectable range by applying force toward the target detection region.

[13] The insertion portion detection system according to (1), characterized by comprising more than one sensor unit.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An insertion portion detection device for detecting a displacement of an insertion portion inserted into an insertion target, wherein an outer circumferential surface of the insertion portion comprises an optical pattern, the insertion portion detection device comprising:

a light source configured to emit a measuring beam to the outer circumferential surface of the insertion portion;

an optical pattern sensor configured to:

receive reflected light from the outer circumferential surface of the insertion portion; and sequentially acquire, from the received reflected light, at least:

first image data of a first image at a first time, wherein the first image includes at least a portion of the optical pattern; and second image data of a second image at a second time, wherein the second image includes the at least a portion of the optical pattern; and a displacement amount calculation circuit configured to:

compare the first image data and the second image data to calculate an optical pattern displacement of the portion of the optical pattern included in the first image acquired at the first time and the portion of the optical pattern included in the second image acquired at the second time; and detect the displacement of the insertion portion between the first time and the second time based on the calculated optical pattern displacement.

2. The insertion portion detection device according to claim 1, wherein the insertion portion is configured to be inserted along an insertion axis into the insertion target, and wherein the displacement amount calculation circuit is configured to calculate, as the optical pattern displacement:

an optical pattern axial displacement along the insertion axis of the portion of the optical pattern included in the first image acquired at the first time and the portion of the optical pattern included in the second image acquired at the second time; and an optical pattern rotational displacement about the insertion axis of the portion of the optical pattern included in the first image acquired at the first time and the portion of the optical pattern included in the second image acquired at the second time, and wherein the displacement amount calculation circuit is configured to detect:

an insertion amount of the insertion portion between the first time and the second time based on the optical pattern axial displacement; and a rotation amount of the insertion portion between the first time and the second time.

3. The insertion portion detection device according to claim 1 wherein the measuring beam emitted from the light source is coherent light.

4. The insertion portion detection device according to claim 1 wherein the optical pattern sensor is configured to:

generate a first speckle pattern from the first image data, wherein the first speckle pattern represents the at least the portion of the optical pattern included in the first image; and generate a second speckle pattern from the second image data, wherein the second speckle pattern represents the at least the portion of the optical patter included in the second image, and wherein the displacement amount calculation circuit is configured to compare the first speckle pattern generated from the first image data and the second speckle pattern generated from the second image data to calculate the optical pattern displacement.

5. The insertion portion detection device according to claim 1, wherein the optical pattern sensor comprises light receiving elements arrayed in matrix form in a two-dimensional direction.

6. The insertion portion detection device according to claim 1, further comprising:

a movement control mechanism configured to dispose at least the light source and the optical pattern sensor in alignment with or in the vicinity of an insertion hole of the insertion target through which the insertion portion is inserted into the insertion target.

7. The insertion portion detection device according to claim 6, wherein the insertion portion is configured to be inserted along an insertion axis into the insertion target, wherein the movement control mechanism comprises a housing, wherein a part of the housing defines an opening configured to pass the insertion portion, and wherein the part of the housing that defines the opening is configured to:

be inserted in the insertion hole of the insertion target; or be arranged adjacent the insertion hole of the insertion target along the insertion axis.

8. The insertion portion detection device according to claim 1, the device comprising one or more position limiters configured to limit, to a range detectable by the sensor unit, movement of a target detection region in a direction perpendicular to the direction in which the movement is detected as an insertion amount of the insertion portion, the target detection region being a region on the outer circumferential surface of the insertion portion where the image data is to be acquired.

9. The insertion portion detection device according to claim 8, the position limiters have groove structures to hold the insertion portion in between, and the position limiters limit the movement of the target detection region by catching the insertion portion in at least two groove structures.

10. The insertion portion detection device according to claim 8 the position limiters are configured to adjust the space between the position limiters and the insertion portion in accordance with the diameter of the insertion portion.

11. The insertion portion detection device according to claim 1, the device comprising a sensor distance maintaining unit configured to move the position of the sensor unit to maintain, within a range detectable by the sensor unit, the distance between the optical pattern detection unit and a target detection region which is a region on the outer circumferential surface of the insertion portion where the image data is to be acquired.

12. The insertion portion detection device according to claim 11, the sensor distance maintaining unit is a spring structure which moves the sensor unit to the detectable range by applying force toward the target detection region.

13. The insertion portion detection device according to claim 1, the device comprising more than one sensor unit.

14. An insertion portion detection system comprising:

the insertion portion detection device according to claim 1;

an input device configured to receive an inputted instruction;

a computer configured to, in response to the inputted instruction, control the light source, the optical pattern sensor, and the displacement amount calculation circuit to detect the displacement of the insertion portion between the first time and the second time; and a monitor configured to be controlled by the computer to display information indicating the displacement of the insertion portion between the first time and the second time detected by the displacement amount calculation circuit.

* * * * *